United States Patent
Abuhamad

(10) Patent No.: US 9,603,602 B2
(45) Date of Patent: Mar. 28, 2017

(54) UTERINE COMPRESSION DEVICES AND METHODS

(71) Applicant: Eastern Virginia Medical School, Norfolk, VA (US)

(72) Inventor: Alfred Z. Abuhamad, Norfolk, VA (US)

(73) Assignee: Eastern Virginia Medical School, Norfolk, VA (US)

(*) Notice: Subject to any disclaimer, the term of this patent is extended or adjusted under 35 U.S.C. 154(b) by 0 days.

(21) Appl. No.: 15/273,418

(22) Filed: Sep. 22, 2016

(65) Prior Publication Data

US 2017/0007436 A1     Jan. 12, 2017

Related U.S. Application Data

(60) Division of application No. 14/846,330, filed on Sep. 4, 2015, which is a continuation of application No. PCT/US2014/021372, filed on Mar. 6, 2014.

(60) Provisional application No. 61/773,376, filed on Mar. 6, 2013.

(51) Int. Cl.
*A61B 17/00* (2006.01)
*A61B 17/132* (2006.01)
*A61F 5/34* (2006.01)
*A61F 5/03* (2006.01)

(52) U.S. Cl.
CPC ............ *A61B 17/1325* (2013.01); *A61F 5/03* (2013.01); *A61F 5/34* (2013.01)

(58) Field of Classification Search
CPC .............. A61B 17/1325; A61B 17/135; A61B 17/1327; A61B 17/1322; A61B 17/132

USPC .................................................. 606/201–203
See application file for complete search history.

(56) References Cited

U.S. PATENT DOCUMENTS

| | | | |
|---|---|---|---|
| 4,270,527 A | 6/1981 | Peters et al. | |
| 4,355,632 A | 10/1982 | Sandman | |
| 4,989,615 A | 2/1991 | Hochberg | |
| 5,057,117 A | 10/1991 | Atweh | |
| 5,174,281 A | 12/1992 | Lee | |

(Continued)

FOREIGN PATENT DOCUMENTS

| | | | |
|---|---|---|---|
| KR | 100904045 B1 * | 6/2009 | |
| WO | WO-01/89433 | 11/2001 | |
| WO | WO-2013/122681 | 8/2013 | |

OTHER PUBLICATIONS

Cook Medical "Managing PPH: A Physician's Perspective on the Cook Bakri ® Postpartum Balloon" V2.3.6, Jul. 1, 2015, downloaded from <https://www.cookmedical.com/reproductive-health/tag/bakri-postpartum-balloon/> (2 pages; accessed Feb. 13, 2016).

(Continued)

*Primary Examiner* — Katherine M Shi
(74) *Attorney, Agent, or Firm* — Wilmer Cutler Pickering Hale and Dorr LLP

(57) ABSTRACT

Disclosed are devices for reducing postpartum hemorrhage, including a belt having a fastener for securing the belt around a patient's body, a bladder being inflatable with air and adapted to be placed over the patient's abdomen for applying selective external pressure to the patient's uterus, a manual pump operably connected to the bladder to change air pressure of the bladder, and a pressure gauge for indicating the air pressure. Methods for using the devices are also disclosed.

4 Claims, 6 Drawing Sheets

(56) References Cited

U.S. PATENT DOCUMENTS

| | | | |
|---|---|---|---|
| 5,259,397 A | 11/1993 | McCabe | |
| 5,368,547 A | 11/1994 | Polando | |
| 5,464,420 A | 11/1995 | Hori et al. | |
| 5,514,155 A | 5/1996 | Daneshvar | |
| 5,645,563 A | 7/1997 | Hahn et al. | |
| 5,779,657 A | 7/1998 | Daneshvar | |
| 5,792,173 A | 8/1998 | Breen et al. | |
| 5,871,499 A * | 2/1999 | Hahn | A61B 17/42 600/588 |
| 6,626,856 B2 | 9/2003 | Manoach | |
| 6,629,942 B1 | 10/2003 | Tubbs | |
| 2004/0068290 A1 | 4/2004 | Bates et al. | |
| 2006/0173486 A1 | 8/2006 | Burke et al. | |
| 2008/0215031 A1 | 9/2008 | Belfort et al. | |
| 2010/0286735 A1 | 11/2010 | Garfield et al. | |
| 2011/0015708 A1 * | 1/2011 | Lee | A61F 5/0193 607/112 |
| 2012/0172898 A1 * | 7/2012 | Pedrick | A61B 17/42 606/151 |
| 2013/0304112 A1 | 11/2013 | Ting et al. | |
| 2013/0310628 A1 | 11/2013 | Chisena et al. | |
| 2013/0310872 A1 | 11/2013 | Croushorn et al. | |
| 2015/0209218 A1 | 7/2015 | Rego | |

OTHER PUBLICATIONS

International Search Report and Written Opinion for International Application No. PCT/US2014/021372 dated Jun. 20, 2014 (8 pages).
Soltan et al., "El-Menia Air Inflated Balloon in Controlling Atonic Post Partum Hemorrhage," International Journal of Health Sciences, Qassim University, vol. 1, No. 1, pp. 53-59 (Jan. 2007).
Extended European Search Report for European Patent Application No. 14759539.1 dated Jun. 29, 2016 (6pages).

* cited by examiner

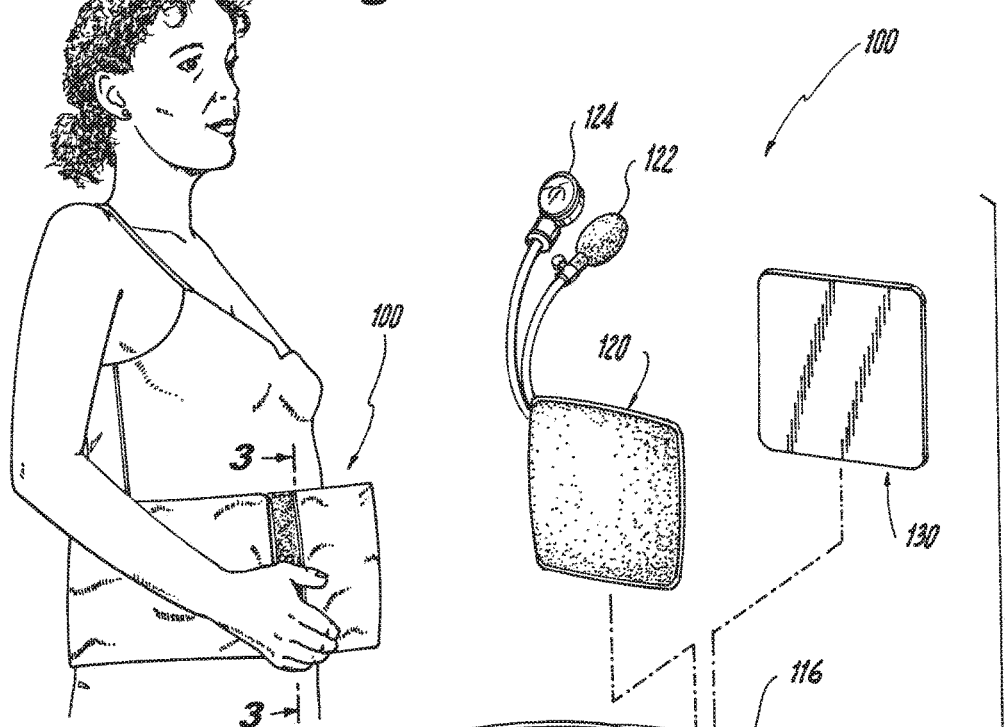
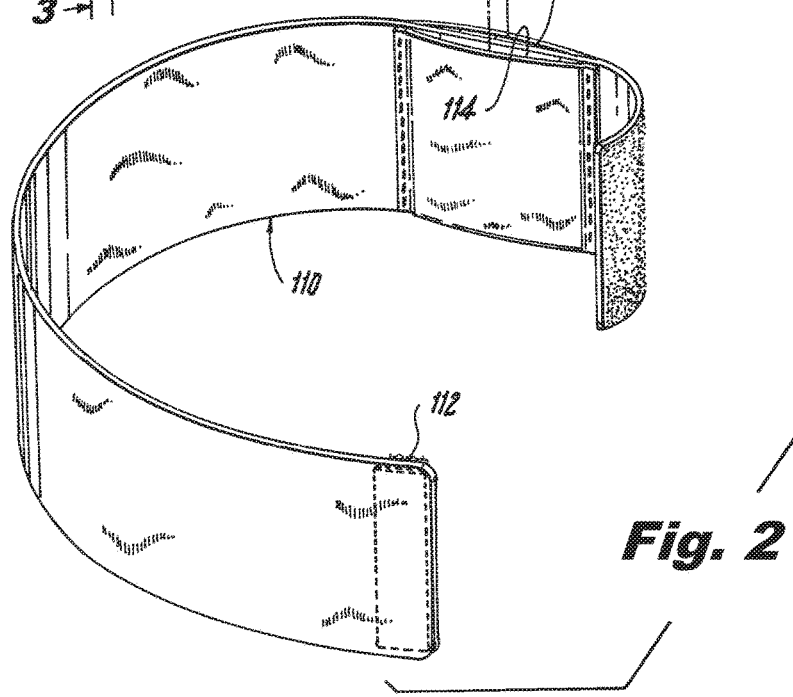

UTERINE COMPRESSION DEVICES AND METHODS

CROSS-REFERENCE TO RELATED APPLICATIONS

This application is a Divisional of U.S. application Ser. No. 14/846,330, filed Sep. 4, 2015, which is a Continuation of International Application No. PCT/US14/21372, filed Mar. 6, 2014, which claims benefit under 35 U.S.C. §119(e) of U.S. Provisional Patent Application No. 61/773,376, entitled "Uterine Compression Devices and Methods," filed Mar. 6, 2013, the disclosures of which are expressly incorporated by reference herein in their entirety.

BACKGROUND

Postpartum hemorrhage, or hemorrhage after delivery, is a leading cause of maternal morbidity, and contributes to about 550,000 maternal deaths annually. Uterine atony is a prevalent cause of postpartum hemorrhage, and accounts for about 70% of maternal deaths. Other causes of postpartum hemorrhage include trauma, retained placenta, and coagulopathy, which is a clotting disorder. Uterine atony is a condition in which the uterus is unable to contract and may lead to continuous bleeding.

Typically, the uterus expands to accommodate the growing fetus during pregnancy, and contracts during labor to allow the fetus and placenta to pass through the birth canal during delivery. After delivery, contraction compresses the veins and arteries that run through the uterus, thus resulting in cessation of bleeding. However, during uterine atony, there is a loss of tone in the uterine musculature, and this lack of uterine contraction can cause hemorrhaging.

There is a need for devices and methods that address the serious consequences of postpartum hemorrhage.

SUMMARY OF THE INVENTION

The disclosure relates to devices and methods to reduce or treat postpartum hemorrhage.

In one aspect, devices for reducing postpartum hemorrhage are disclosed, comprising a belt having a fastener for securing the belt around a patient's body, a bladder being inflatable with air and adapted to be placed over the patient's abdomen for applying selective external pressure to the patient's uterus, an inflatable pump operably connected to the bladder to change air pressure of the bladder, and a pressure gauge for indicating the air pressure.

In another aspect, methods for reducing postpartum hemorrhage are disclosed, comprising a) providing a device comprising a belt having a fastener for securing the belt around a patient's body, a bladder being inflatable with air and adapted to be placed over the patient's abdomen for applying selective external pressure to the patient's uterus, an inflatable pump operably connected to the bladder to change air pressure of the bladder, and a pressure gauge for indicating the air pressure; b) placing the device around the patient's body; c) inflating the bladder using the manual pump such that the bladder applies selective external pressure to the patient's uterus; and d) changing the pressure to induce uterine contractions.

BRIEF DESCRIPTION OF THE DRAWINGS

The foregoing and other objects of the present invention, the various features thereof, as well as the invention itself, may be more fully understood from the following description, when read together with the accompanying drawing. The drawing is presented for the purpose of illustration only and is not intended to limit the invention.

FIG. 1 illustrates one embodiment of a device for reducing or treating postpartum hemorrhage in accordance with aspects of the present invention FIG. 2 is a perspective view of the device of FIG. 1.

DETAILED DESCRIPTION

Figure 3:
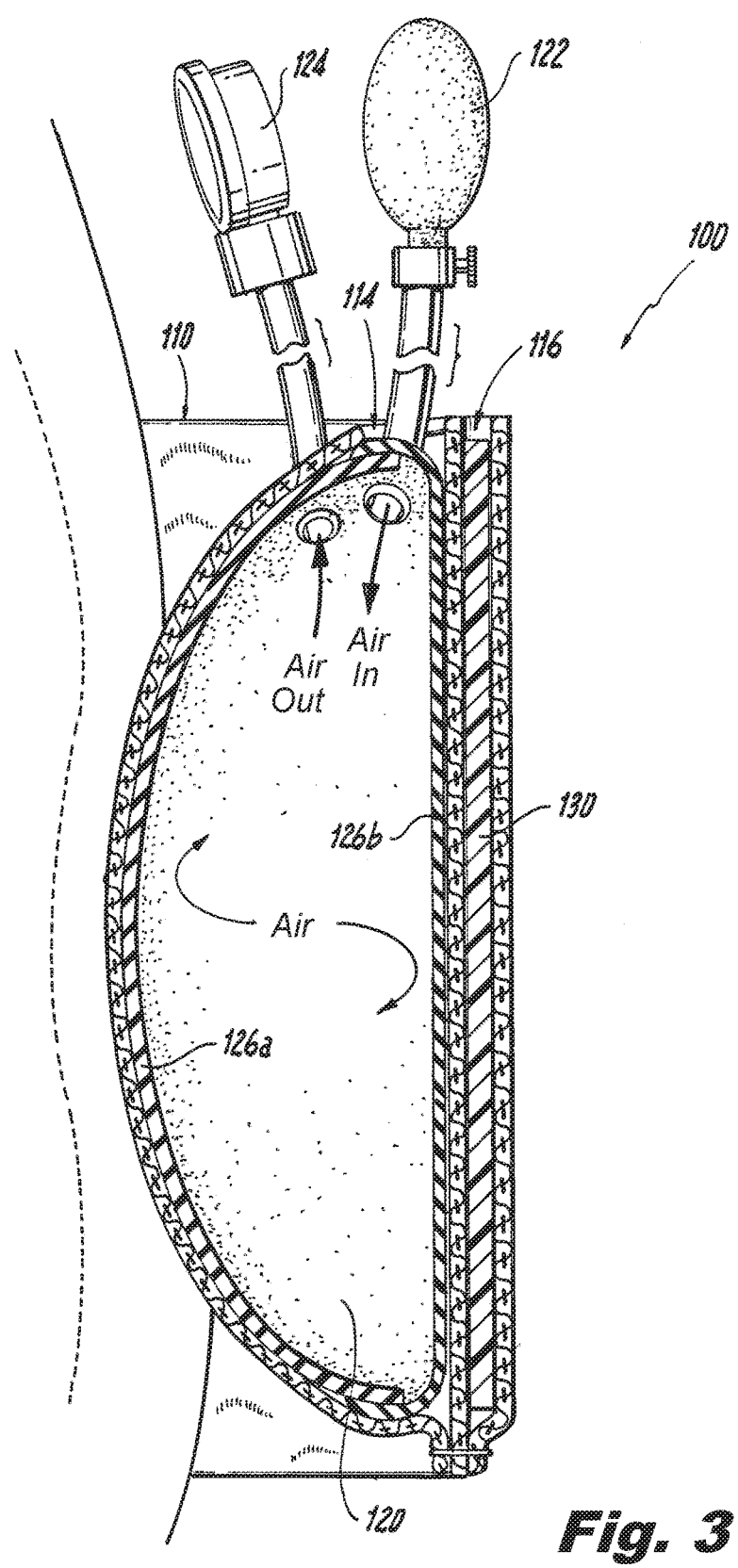
FIG. 3 is a cross-sectional view of the device of FIG. 1 positioned and inflated for use.

As will be apparent to one of ordinary skill in the art from a reading of this disclosure, the disclosed subject matter can be embodied in forms other than those specifically disclosed herein. The particular embodiments described herein are, therefore, to be considered as illustrative and not restrictive. Those skilled in the art will recognize, or be able to ascertain, using no more than routine experimentation, numerous equivalents to the specific embodiments described herein.

The instant disclosure provides devices and methods to treat postpartum hemorrhage that comprise a belt having a fastener for securing the belt around a patient's body, a bladder being inflatable with air and adapted to be placed over the patient's abdomen for applying selective external pressure to the patient's uterus, an inflatable pump operably connected to the bladder to change air pressure of the bladder, and a pressure gauge for indicating the air pressure. In some embodiments, the bladder is in the shape of the postpartum uterus.

Known methods to reduce postpartum hemorrhage include mechanical and electrical stimulation to increase uterine contraction. Uterine massage involves applying external and internal pressure on the uterus to help minimize bleeding. Devices known in the art are inserted vaginally and compress the uterus internally to reduce postpartum hemorrhage.

The instant disclosure addresses limitations in the art by providing devices and methods that are simple to use, and that reduce postpartum hemorrhage through external compression of the uterus. The disclosed devices and methods are useful in developing countries with a high incidence of death from postpartum hemorrhage, and where access to surgical facilities is scarce. The disclosed devices and methods can be used to stabilize a patient suffering from postpartum hemorrhage for a period of time sufficient for transporting the patient from a remote location to a facility for further medical treatment.

Conventional emergency trauma devices are not suitable for such long-distance transport because they work by cutting off blood flow to the entire area, usually by compressing the entire pelvis or the entire lower half of the patient's body. This significantly limits the amount of time that these trauma devices can be safely worn without potential damage to the patient. In contrast, the present device is shaped and positioned to apply selective external pressure to the uterus without cutting off all blood flow to the pelvis. The selective nature of the pressure applied reduces the discomfort and the potential damage to the patient and allows the device to be safely worn for longer periods of time until further medical care is available.

In some embodiments, the disclosed devices use external compression of the uterus with an inflatable bladder, which, when inflated, expands towards the abdomen and compresses the uterine muscle and uterine vasculature. In some embodiments, when the belt is positioned on the body, the bladder is located centrally in the lower abdomen over the postpartum uterus. When the bladder is inflated, the pressure within the bladder expands ventrally towards the maternal abdomen, thus compressing the postpartum uterus. This uterine compression results in increased uterine contractions and reduces or stops bleeding.

The disclosed devices and methods can be used alone or conjunction with direct mechanical stimulation of the uterus, as well as with other devices and methods to reduce or treat postpartum hemorrhage.

FIG. 1 illustrates one embodiment of a device 100 for reducing or treating postpartum hemorrhage, which is shown being worn in position around a patient's midsection to apply selective external pressure to the uterus.

FIG. 2 shows the device 100 in further detail. The device 100 as illustrated includes a belt 110 with an adjustable fastener 112 and pockets 114, 116.

In some embodiments, the belt 110 may be made from materials including, but not limited to, leather, plastic, rubber, or rubber-like materials. Various coatings can be added to the surfaces of the belt 110 to change their flexibility or rigidity. In some embodiments, the belt 110 can be secured to the body using various fastening means known in the art, including, but not limited to, straps, buttons, fasteners, connectors, tapes, adhesives, and interlocking fabric materials, such as Velcro.

Each of the pockets 114, 116 of the belt may be made of the same material or a different material, and may be integral with the belt or attached to it by stitching, adhesive, or another means. The pockets 114, 116 may be detachable; in some embodiments one or both of the pockets may include webbing or other material flexible enough to accommodate the components of the device 100.

As shown in FIG. 2, the device 100 further includes an inflatable bladder 120 which can optionally be removably placed in the internal pocket 114 of the belt 110. The bladder 120 is manually operated by means of a pump 122 and pressure gauge 124 in communication therewith. Other means of inflation are known in the art. In some embodiments, the bladder has a soft, flexible ventral surface and a hard, semi-rigid dorsal surface. Various materials can be used in the disclosed devices. The ventral surface that comes in contact with the skin can be made from materials including, but not limited to, a soft fabric and woven materials such as cotton or nylon. Various coatings can be added to the surfaces of the bladder to change their flexibility or rigidity.

The bladder 120 size and shape may partially determine the operation of the disclosed devices. These size ratios can be varied, which can determine the range of pressures that can be exerted on the uterus. In some embodiments, the amount of air compression is changed during operation of the device to provide safe compression of the uterus. In some embodiments, the bladder is in the shape of the postpartum uterus.

The device 100 further includes an external plate 130 which can be removably placed in the external pocket 116 of the belt 110. The plate 130 may be made of any material with sufficient rigidity to provide support for the bladder 120, such as a metal or hard plastic. Although the plate 130 is shown as generally rectangular and planar, it will be understood that plates of additional contour and shape may be included. In some implementations, the plate 130 may be curved to provide additional structural support near the center of the bladder 120. The outer contour of the plate 130 may be shaped to match the bladder 120.

The device is placed around the patient's midsection with the bladder positioned over the patient's abdomen to provide external pressure to the uterus when inflated. FIG. 3 is a cross-sectional view showing the device 100 in use. As shown, the bladder 120 is inflated by means of air entering it from the pump 122, which may be a manual pump similar to that used in a sphygmomanometer. The bladder 120 is also in fluid communication with the pressure gauge 124, which may include annotations (not shown) that correspond to the amount of pressure exerted against the abdomen to selectively compress the uterus. A medical professional may use the pressure gauge 124 to determine how much to inflate or deflate the bladder 120 based on the condition of the patient.

As shown in FIG. 3, the bladder 120 may have an inner wall 126a and an outer wall 126b, which may be comprised of different materials. The inner wall 126a may be a more flexible material than the outer wall 126b such that, upon inflation, the bladder 120 mainly expands towards the inner wall 126. In some implementations, both walls of the bladder 120 may be made of the same material, and in some embodiments may also be made of a single piece rather than multiple pieces. When the walls of the bladder 120 are not made of different material, the bladder 120 may still inflate inward due to the flexible material of the inner belt pocket 114 against the inner wall 126a, combined with the rigid material of the plate 130 against the outer wall 126b.

Figure 4:
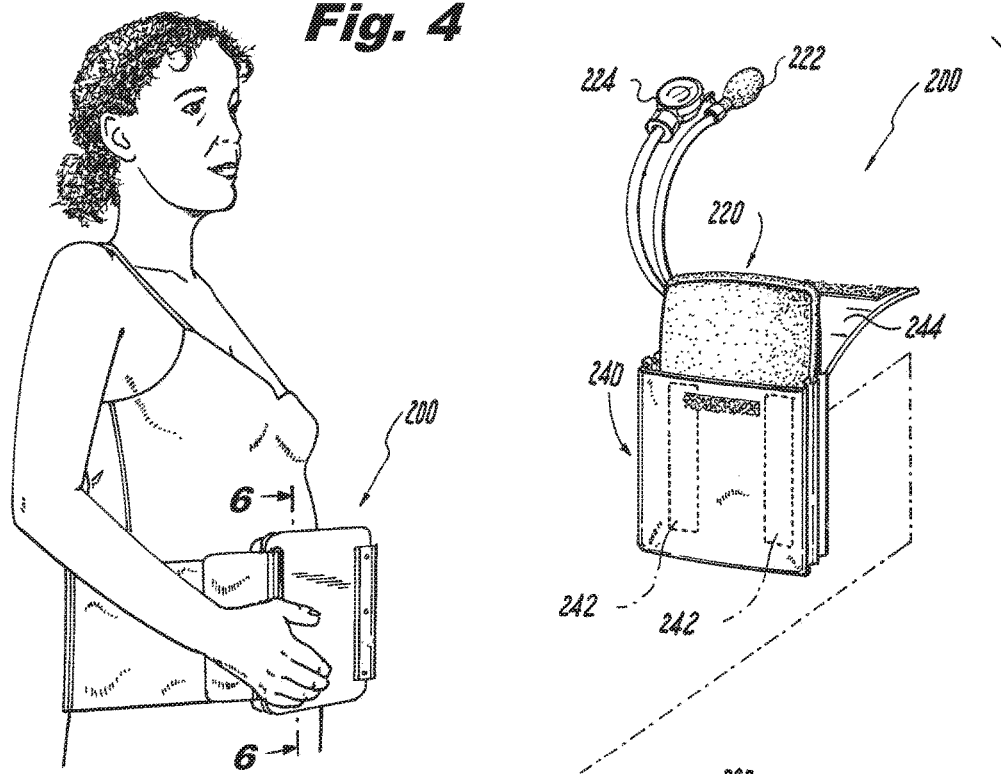
FIG. 4 illustrates another embodiment of a device for reducing or treating postpartum hemorrhage in accordance with aspects of the present invention
Figure 5:
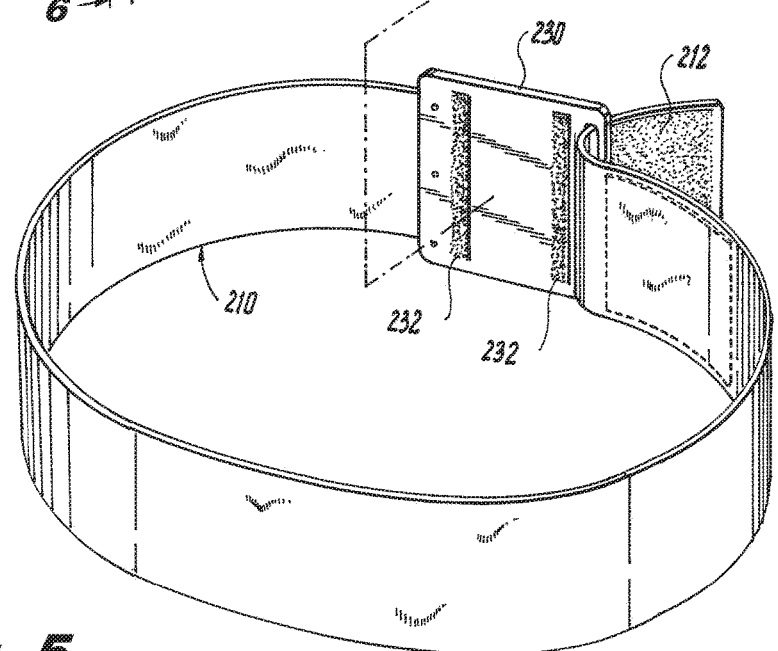
FIG. 5 is a perspective view of the device of FIG. 4.
Figure 6:
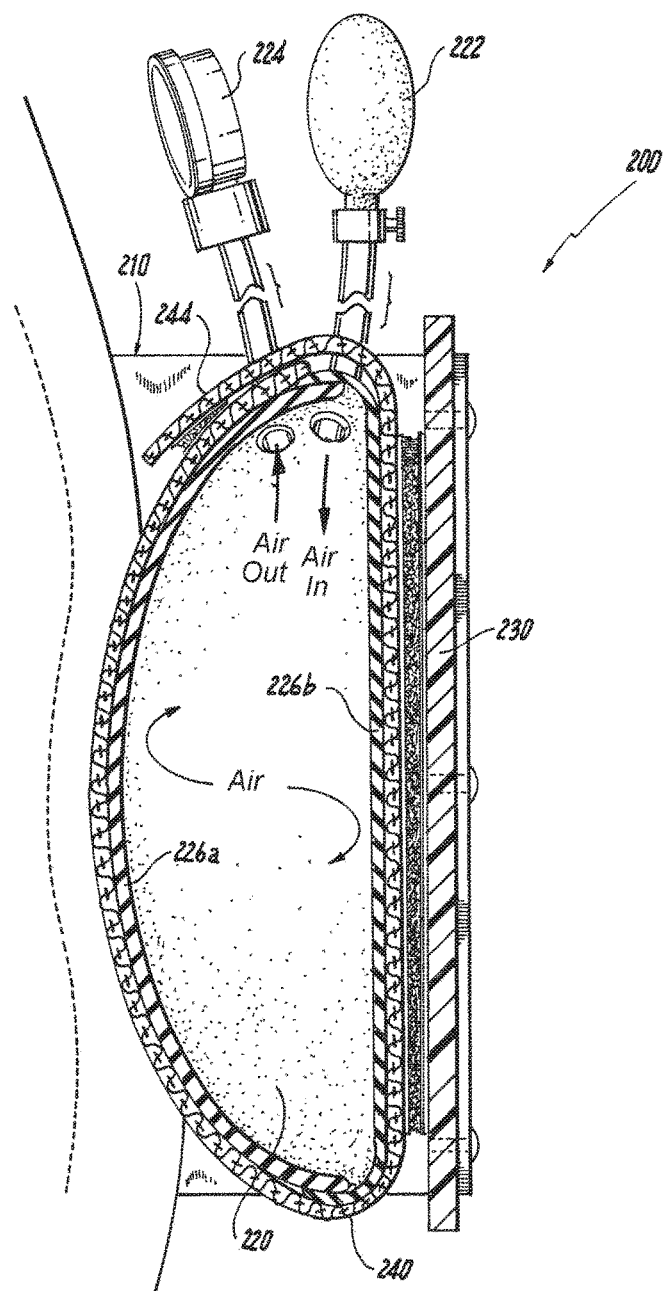
FIG. 6 is a cross-sectional view of the device of FIG. 4 positioned and inflated for use.

FIGS. 4-6 illustrate a different embodiment of a device 200 in accordance with the disclosure herein, and corresponding numbers generally indicate corresponding parts between the device 100 and device 200 as detailed herein.

As shown, a belt 210 may include a plate 230 as a permanently affixed part of the belt 210. The belt 210 may fasten by threading through the plate 230 and attaching with fasteners 212 as shown. In this embodiment, the device 200 includes a detachable pouch 240 in which the inflatable bladder 220 is placed. The pouch 240 in turn fastens to the inner surface of the plate 230 by means of fasteners 232, 242. The pouch 240 may further include a flap 244 that allows it to close, securing the inflatable bladder 220. In some embodiments, the flap 244 may be sized and positioned so as to allow access to the pump 222 and pressure gauge 224 even when closed.

FIG. 6 is a cross-section showing the inflated bladder 220 again providing selective pressure against a patient's abdomen. As described above, the bladder 220 may again include internal and external walls 226a, 226b which may be made of the same or different materials. Here, it is the material of the pouch 240 that accommodates the expanding inner wall 226a of the bladder 220, and it is the rigid material of the plate 230 that provides support for the outer wall 226b.

Figure 7:
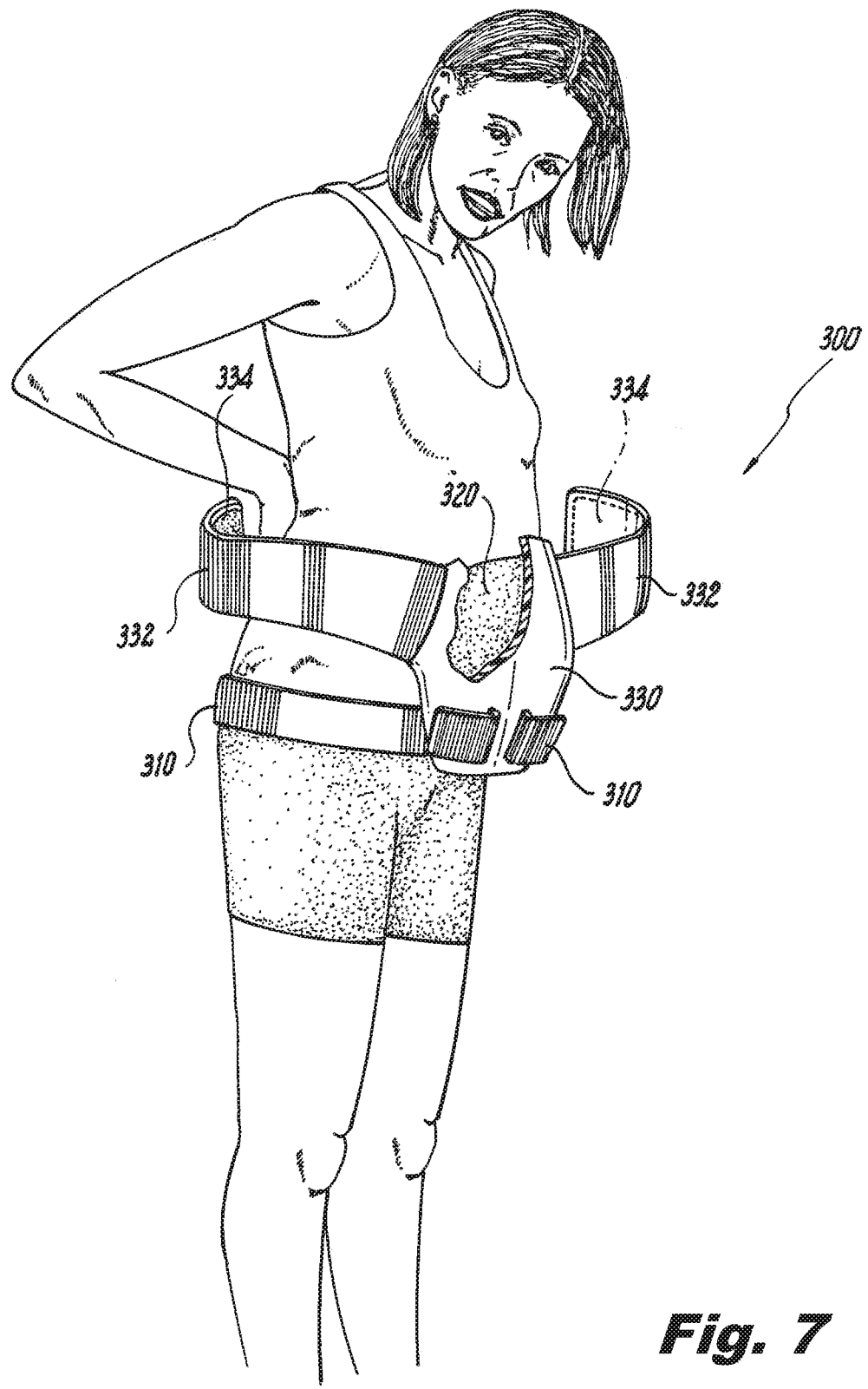
FIG. 7 illustrates a further embodiment of a device for reducing or treating postpartum hemorrhage in accordance with aspects of the present invention.

FIG. 7 illustrates a further embodiment of a device 300 in accordance with the disclosure herein. As shown, a device 300 may include an armored belly plate 330 that is contoured to fit around a patient's abdomen. In this embodiment, the inflated bladder 320 is enclosed by the armored plate 330. The shape of the bladder 320 may be customized to fit the contours of the plate 330, or may instead represent a more generic shape. The contours of the armored plate 330 direct the pressure of the inflated bladder 320 into the patient's abdomen as desired.

The armored belly plate 330 may include attached straps 332 with fasteners 334, and in some embodiments may also include one or more supplemental adjustable straps 310. The adjustable straps 310 may include any of the variations in structure or material discussed above with respect to the belt 110, 210. When properly adjusted, the lower adjustable straps 310 may increase the compression on the patient's lower abdomen, allowing an additional point of adjustment in the amount of selective pressure applied to the upper and lower parts of the uterus.

Figure 8:
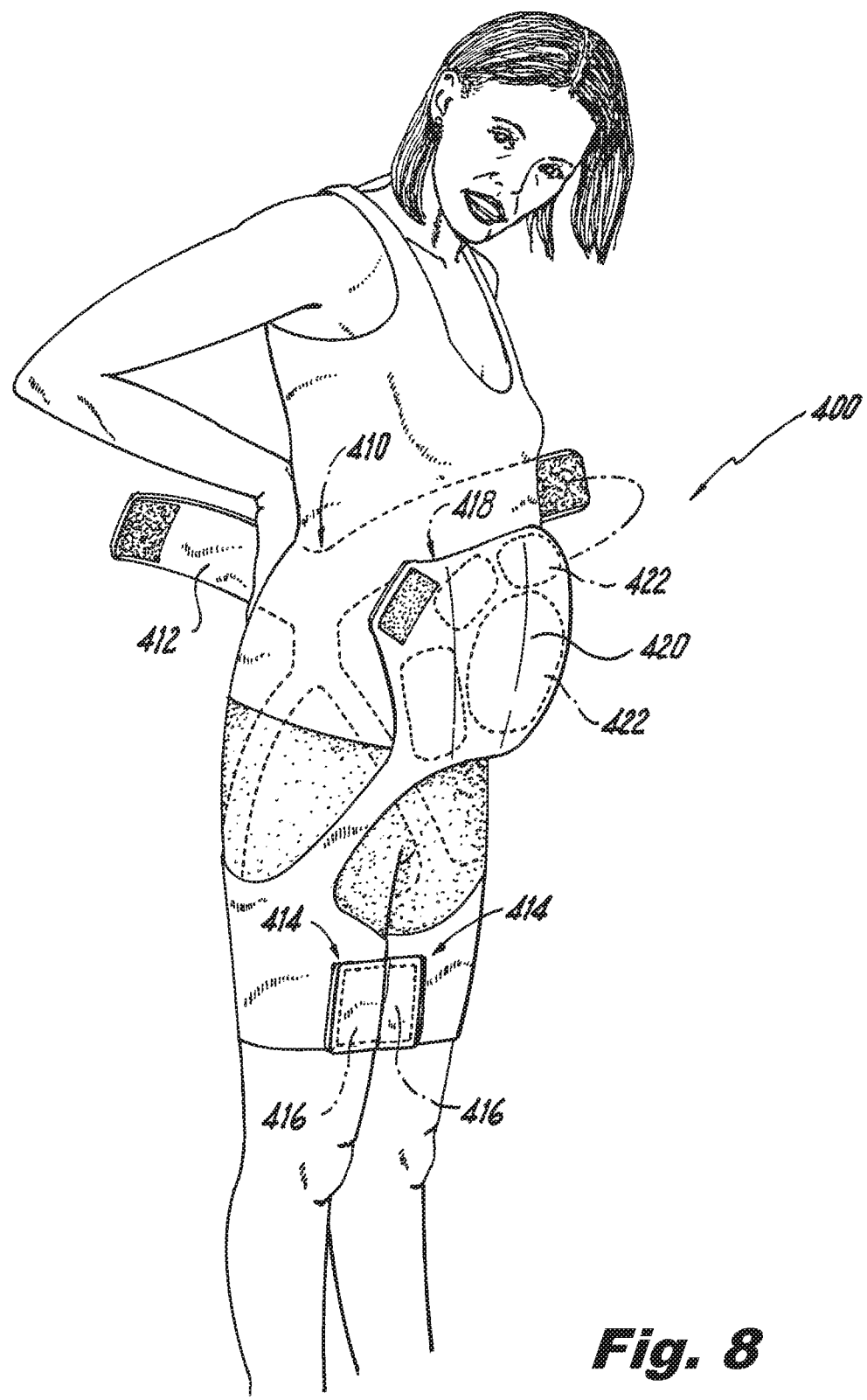
FIG. 8 illustrates another embodiment of a device for reducing or treating postpartum hemorrhage in accordance with aspects of the present invention.

FIG. 8 illustrates another embodiment of a device 400 in accordance with the disclosure herein. As shown, a device 400 may include a harness 410, with an upper adjustable strap 412 and anchor cuffs 414 with adjustable fasteners 416. The harness 410 may include a front inner section 418 suitable to accommodate one or more inflatable bladders 422 as further described therein. In some implementations, the front inner section 418 may be configured to accommodate multiple different configurations of bladders 422 as necessary to suit the particular needs of each patient. The front outer section 420 of the harness may be flexible, or alternatively may be made of a rigid or semi-rigid material to further direct the selective pressure from the inflatable bladder or bladders 422 toward the patient's abdomen.

Devices described herein may include considerable customization, and different parts may be selected for different patients as needed. For instance, the belt may be selected according to the patient's full waist size, while the inflatable bladder may be selected to provide selective pressure according to the patient's condition. Devices, particularly those provided for use in emergency trauma situations distant from hospitals, may also provide substantial customization and size and shape within a device by providing a broad range of fastening positions for the belt.

In some implementations, the bladder size may also be adjustable. Multiple bladders may be used, or alternatively a bladder may include multiple chambers or baffles which allow for the pressure to be directed to different regions of the abdomen. In some implementations, the inflatable bladder may include multiple internal inflatable chambers surrounded by a single outer material for accommodation and shaping of the pressure produced by the bladder. Where more than one bladder or more than one inflatable chamber is used, each may include its own pump, or the multiple bladders or chambers may be in fluid communication such that a single action may be used to inflate more than one.

In some implementations, multiple adjustable belts may be used. Each belt may be adjusted to provide an appropriate fit and the right amount of compression in conjunction with one or more inflated bladders. The material and fastenings of each belt may be different as discussed above with respect to belt 110.

In some implementations, additional rigid pieces may be included in addition to the external plate pressing against the bladder. A rigid backboard may be used to anchor the device and prevent excessive pressure in specific areas of the patient's back. Rigid side-pieces may also be used to further stabilize the device and help prevent bunching up or shifting of components during use. Any such rigid pieces may be contoured to the patient's body and therefore may come in a variety of shapes and sizes. The rigid pieces may include attached straps or may be designed to attach to other components of the device.

Although the exemplary embodiments use a hand pump, it will be understood that a variety of pumps, both manual and machine-driven, may be used. Similarly, any appropriate pressure gauge may be used in place of the analog gauge shown. If an electronic gauge is shown, an alarm or other alert mechanism may be included when a predetermined pressure is reached. One of ordinary skill will recognize that some implementations may allow the pressure gauge and pump to share a single opening in the bladder rather than being separate. In some implementations, one or more check valves or other pneumatic features may be included to allow the pump, the pressure gauge, or both to be removed from the bladder once the bladder is inflated. Further features such as pressure release valves may also be included to prevent over-inflation of the bladder. In place of a pump, a pressurized cartridge may be used to inflate the bladder. The bladder may also be inflated with a fluid other than air, such as carbon dioxide.

Postpartum hemorrhage may be treated or prevented in a patient by use of the disclosed device. The belt is fastened around the patient's body such that the bladder contacts the abdomen in the appropriate location to provide pressure to the upper section of the uterus, and the bladder is inflated to provide pressure to the appropriate section. The pump and pressure gauge allow for the monitoring and adjusting of the pressure as necessary.

During uterine atony, the uterus fails to contract, and this can cause postpartum hemorrhage. In the disclosed methods, increasing compression of the uterus induces uterine contractions and, thus, reduces or treats postpartum hemorrhage. In some embodiments, after a patient's condition is stabilized and the bleeding rate decreases to a sufficient predetermined level, compression on the uterus can be decreased. If uterine bleeding restarts, then compression can be restarted. In some embodiments, a medical provider monitors the patient's condition and increases or decreases compression as needed to reduce or treat postpartum hemorrhage.

What is claimed is:

1. A method for reducing postpartum hemorrhage, comprising:
    providing a device including:
        a belt having a fastener for securing the belt around a patient's body,
        a bladder being inflatable with air and adapted to be placed over the patient's abdomen for applying selective external pressure to the patient's postpartum uterus,
        a manual pump operably connected to the bladder to change air pressure of the bladder; and a pressure gauge for indicating the aft pressure;
    placing the device around the patient's body;
    inflating the bladder using the manual pump such that the bladder expands ventrally inwards against the patient's abdomen thus applying selective external pressure to the patient's postpartum uterus; and
    changing the pressure to induce uterine contractions.

2. The method of claim 1 wherein the device is left in place around the patient's body continuously for multiple hours.

3. The method of claim 1,
    wherein the steps are carried out in response to diagnosing the patient with uterine atony, and
    wherein the induced uterine contractions result in a reduction in hemorrhaging by the patient.

4. The method of claim 1, wherein the changing the pressure to induce uterine contractions comprises determining a goal pressure, operating the pump to change the pressure, and monitoring the pressure gauge to determine when the goal pressure is achieved.

* * * * *